(12) United States Patent
Liu et al.

(10) Patent No.: US 11,834,645 B2
(45) Date of Patent: Dec. 5, 2023

(54) RESPIRATOR, MEASUREMENT DEVICE AND MEASURING METHOD FOR MEASURING RESPIRATORY RATE OF BIOFILM

(71) Applicant: Jinan University, Guangzhou (CN)

(72) Inventors: Guoqiang Liu, Guangzhou (CN); Zichuan Lu, Guangzhou (CN)

(73) Assignee: JINAN UNIVERSITY, Guangdong (CN)

( * ) Notice: Subject to any disclaimer, the term of this patent is extended or adjusted under 35 U.S.C. 154(b) by 995 days.

(21) Appl. No.: 16/631,462

(22) PCT Filed: Sep. 7, 2018

(86) PCT No.: PCT/CN2018/104513
§ 371 (c)(1),
(2) Date: Jan. 16, 2020

(87) PCT Pub. No.: WO2020/042211
PCT Pub. Date: Mar. 5, 2020

(65) Prior Publication Data
US 2021/0222113 A1    Jul. 22, 2021

(30) Foreign Application Priority Data
Aug. 28, 2018 (CN) .......................... 201810990257.4

(51) Int. Cl.
*C12M 1/00* (2006.01)
*C12M 1/04* (2006.01)
(Continued)

(52) U.S. Cl.
CPC ............ *C12M 41/46* (2013.01); *C12M 23/34* (2013.01); *C12M 23/38* (2013.01); *C12M 27/04* (2013.01); *C12M 29/20* (2013.01); *C12Q 1/02* (2013.01)

(58) Field of Classification Search
CPC ...... C12M 41/46; C12M 23/34; C12M 23/38; C12M 27/04; C12M 29/20; C12M 25/20;
(Continued)

(56) References Cited

U.S. PATENT DOCUMENTS

| 5,604,297 A | 2/1997 | Seiden et al. |
| 6,416,994 B1 * | 7/2002 | Uruga ....................... C02F 3/28 |
| | | 435/287.5 |

(Continued)

FOREIGN PATENT DOCUMENTS

| CN | 102121917 | 7/2011 |
| CN | 206395922 | 8/2017 |

(Continued)

OTHER PUBLICATIONS

International Search Report dated May 31, 2019 From the International Searching Authority Re. Application No. PCT/KR2018/104513. (5 Pages).

*Primary Examiner* — Liban M Hassan
(74) *Attorney, Agent, or Firm* — MUNCY, GEISSLER, OLDS & LOWE, P.C.

(57) ABSTRACT

A respirator for measuring a respiratory rate of a biofilm includes a body, a carbon dioxide absorption tube and a perforated partition disposed in an interior of the body. The perforated partition divides the interior of the body into an oxygen mass-transfer stir zone including a stirring device and a biofilm reaction zone for placing MBBR fillers. The carbon dioxide absorption tube includes an air vent and contains a solution capable of absorbing $CO_2$. The perforated partition has a first hole corresponding to a middle portion and a lower portion of the perforated partition and acting as a liquid-exchange channel, and a second hole corresponding to an upper portion of the perforated partition and acting as a gas-exchange channel, and the oxygen (Continued)

mass-transfer stir zone is communicated with the biofilm reaction zone through the liquid-exchange channel and the gas-exchange channel.

17 Claims, 3 Drawing Sheets

(51) Int. Cl.
 *C12M 1/34* (2006.01)
 *C12Q 1/02* (2006.01)
(58) Field of Classification Search
 CPC ...... C12M 41/34; C12M 41/48; C12M 25/18; C12M 23/08; C12M 25/02; C12M 29/04; C12Q 1/02; C12Q 2304/44; C02F 3/085; C02F 2209/36; Y02W 10/10
 See application file for complete search history.

(56) References Cited

U.S. PATENT DOCUMENTS

2004/0206699 A1\* 10/2004 Ho .................. C02F 3/301 210/150
2015/0368131 A1\* 12/2015 Garrido Fernandez ............ C12M 23/38 210/264

FOREIGN PATENT DOCUMENTS

| CN | 206768102 | | 12/2017 | |
|----|-----------|---|---------|---|
| DE | 19734154 A1 | \* | 2/1999 | ............ C02F 3/301 |
| JP | 09-135679 | | 5/1997 | |
| JP | 2008194620 A | \* | 8/2008 | |
| KR | 2003065793 A | \* | 8/2003 | ............ C02F 3/301 |
| KR | 10-2006-0033390 | | 4/2006 | |

\* cited by examiner

RESPIRATOR, MEASUREMENT DEVICE AND MEASURING METHOD FOR MEASURING RESPIRATORY RATE OF BIOFILM

RELATED APPLICATIONS

This application is a National Phase of PCT Patent Application No. PCT/CN2018/104513 having International filing date of Sep. 7, 2018, which claims the benefit of priority of Chinese Patent Application No. 201810990257.4 filed on Aug. 28, 2018. The contents of the above applications are all incorporated by reference as if fully set forth herein in their entirety.

FIELD AND BACKGROUND OF THE INVENTION

The present invention relates to the field of sewage treatment, and more particularly, to a respirator, a measurement device and a measuring method for measuring respiratory rate of a biofilm.

As a new-type biofilm reactor, a moving bed biofilm reactor (MBBR) is a modified novel complex biofilm reactor developed from the basis of the fixed bed reactor, the fluidized bed reactor and the biofilter. Such technology requires suspended fillers for use so as to provide a suitable growing environment for the microorganism. It is of great significance for optimization of design and operation of sewage treatment process to determine respiratory dynamic characteristics of the biofilm on the MBBR suspended fillers.

Currently, there are two methods for determining the respiratory dynamic characteristics of the biofilm on the MBBR fillers. One is to directly put the fillers into a respirator, accompanied with magnetic stirring, thereby carrying out a respiratory dynamic test; wherein rotation of a magnetic stirrer would be interfered by the fillers during the measurement and thus oxygen mass transfer is affected; moreover, the biofilm would be scraped off the fillers by the magnetic stirrer and thus structure of the biofilm is damaged and test results are affected; and in fact, the test cannot be achieved. The other is to directly perform a centrifugation to the MBBR fillers, so that the biofilm falls off the fillers and is suspended in the water, and then a respiratory dynamic experiment is carried out according to a conventional approach; such method brings an irreversible damage to the biofilm on the fillers; meanwhile, the falling off of the biofilm leads to a change of a mass-transfer rate of oxygen on the surface of the biofilm on the fillers, and thus respiratory dynamic characteristics of the biofilm cannot be truly reflected.

SUMMARY OF THE INVENTION

In order to overcome at least one defect of the prior art mentioned above, the present invention provides a respirator for measuring a respiratory rate of a biofilm. Used in combination with a conventional respirometer, the respirator can characterize respiratory dynamic characteristics of the biofilm on MBBR fillers, without damage, simply, rapidly and "in situ", also won't damage to the original structure of the biofilm on the MBBR fillers, and reduces damage to the biofilm during the measurement. The measurement results are more accurate.

In order to address the above-mentioned technical problems, the following technical solutions are used in the present invention.

A respirator for measuring a respiratory rate of a biofilm includes a body, a carbon dioxide absorption tube and a perforated partition disposed in an interior of the body. The perforated partition divides the interior of the body into an oxygen mass-transfer stir zone and a biofilm reaction zone, the oxygen mass-transfer stir zone is provided with a stirring device, and the biofilm reaction zone is used for placing MBBR fillers. The carbon dioxide absorption tube is provided with an air vent and contains a solution capable of absorbing $CO_2$, to absorb the $CO_2$ within the body. The perforated partition has a first hole and a second hole, the first hole is located at a middle portion and a lower portion of the perforated partition and acts as a liquid-exchange channel, the second hole is located at an upper portion of the perforated partition and acts as a gas-exchange channel, and the oxygen mass-transfer stir zone is communicated with the biofilm reaction zone through the liquid-exchange channel and the gas-exchange channel.

The perforated partition divides the interior of the body into an oxygen mass-transfer stir zone and a biofilm reaction zone, the oxygen mass-transfer stir zone is provided with a stirring device, the MBBR fillers are placed in the biofilm reaction zone, so that the stirring device would not be interfered by the MBBR fillers, and the biofilm would not be scraped off the MBBR fillers by the stirring device either, thereby avoiding an irreversible damage to the biofilm. The stirring device is used for accelerating dissolution of oxygen in the water. Microorganism attached to the MBBR fillers in the respirator proceeds with a biological reaction in the biofilm reaction zone, consumes the dissolved oxygen in the water and releases $CO_2$ simultaneously. $CO_2$ enters the oxygen mass-transfer stir zone through the gas-exchange channel of the perforated partition, and is absorbed by the solution capable of absorbing $CO_2$ in the carbon dioxide absorption tube. Such configuration on one hand ensures sufficient gas-liquid exchange of the oxygen mass-transfer stir zone and the biofilm reaction zone, and on the other hand prevents damage to the biofilm on the MBBR fillers by the stirring device, and thus it is possible to determine the respiratory dynamic characteristics of the biofilm on the fillers in situ without damage.

Optionally, the solution capable of absorbing $CO_2$ is an alkaline solution such as a KOH solution or a NaOH solution. Different solutions will result in different dosages.

Preferably, the body is provided with a first opening and a second opening, the first opening corresponds to the oxygen mass-transfer stir zone, and the second opening corresponds to the biofilm reaction zone. The first opening is provided with a headspace cap for sealing, and the second opening is provided with a sealing cap for sealing. The stirring device can be taken out of or put into the oxygen mass-transfer stir zone through the first opening. The MBBR fillers can be taken out of or put into the biofilm reaction zone through the second opening. Also direct-contact operation on the corresponding area within the body, such as cleaning, can be carried out through the first opening and/or the second opening. The headspace cap is a cap with a hole in the middle and a gasket (such as a plastic gasket) disposed inside, through which a keen-edged object (such as a tube with a needle at an end) can be inserted into the interior of the respirator but the gas tightness of the respirator is kept. The headspace cap can be customized according to the size, thread and etc. of the first opening of the respirator. When in use, the gas tightness of the respirator can be ensured by screwing down the headspace cap.

As an improvement of the above technical solution, the perforated partition is a cylindrical perforated partition and located at a middle portion of the body, an interior of the cylindrical perforated partition is the oxygen mass-transfer stir zone, between an exterior of the cylindrical perforated partition and the body is the biofilm reaction zone. With such configuration, $CO_2$ which is released by the microbial reaction on the MBBR fillers in the biofilm reaction zone enters the oxygen mass-transfer stir zone in the interior of the cylindrical perforated partition from the exterior of the cylindrical perforated partition, thereby improving a mass-transfer effect.

Optionally, the perforated partition includes two perforated partitions, between the two perforated partitions is the oxygen mass-transfer stir zone, and between the perforated partition and the body is the biofilm reaction zone. When the number of the perforated partitions is two, $CO_2$ which is released by the microbial reaction on the MBBR fillers in the biofilm reaction zones at either side enters the oxygen mass-transfer stir zone in the middle from the biofilm reaction zones at either side, thereby improving the mass-transfer effect. The number of the perforated partition may vary according to practical needs.

As an improvement of the above technical solution, the body is provided with a first opening and two second openings, the first opening corresponds to the oxygen mass-transfer stir zone, the two second openings correspond to two biofilm reaction zones respectively. The first opening is provided with a headspace cap for sealing, and the two second openings are each provided with a sealing cap for sealing. Such configuration is adapted for a respirator including two perforated partitions. Numbers of the first opening and the second opening may vary according to the number of the perforated partition.

Preferably, the carbon dioxide absorption tube is located in the interior of the body and connected to the headspace cap. In such configuration, the carbon dioxide absorption tube is located in the oxygen mass-transfer stir zone. $CO_2$ released from the biofilm reaction zone enters the oxygen mass-transfer stir zone through the gas-exchange channel of the perforated partition, and then $CO_2$ is absorbed by the solution capable of absorbing $CO_2$ in the carbon dioxide absorption tube in the oxygen mass-transfer stir zone. The configuration that the carbon dioxide absorption tube may also be located in the biofilm reaction zone can also achieve test results, and accuracy of the test results would not be affected.

As an improvement of the above technical solution, a bottom of the biofilm reaction zone is further provided with a corner sloping board at a corner of the body. Providing a corner sloping board at the bottom of the biofilm reaction zone can prevent the MBBR fillers in the biofilm reaction zone from forming an oxygen mass-transfer dead angle during the measurement, so as to ensure the measurement process to be effectively performed.

Optionally, the body is cuboid or cylindrical. Whirlpool of water flow in the oxygen mass-transfer stir zone is formed due to the stirring device in the respirator. Water flows all around, and thus the respirator with the cylindrical body is conducive to mixing of the MBBR fillers and the water flow. The respirator with the cylindrical body is more adapted to use the cylindrical perforated partition.

As an improvement of the above technical solution, the first hole includes a plurality of first holes, and the liquid-exchange channel is evenly distributed at the middle portion and the lower portion of the perforated partition. Generally, the liquid-exchange channel has a relatively small size to prevent the MBBR fillers in the biofilm reaction zone from entering the oxygen mass-transfer stir zone, while the gas-exchange channel has a relatively large size to prevent forming a liquid film that prohibits the gas exchange.

Preferably, the stirring device is a magnetic stirrer located at a bottom of the oxygen mass-transfer stir zone. Generation of the whirlpool would not be affected by the magnetic stirrer located at the bottom of the oxygen mass-transfer stir zone.

A measuring device for a respiratory rate of a biofilm includes a respirometer for measuring an oxygen-absorption rate and the above-mentioned respirator, and the respirometer is communicated with an interior of the respirator. Microorganism attached to the MBBR fillers in the respirator proceeds with a biological reaction in the biofilm reaction zone, consumes the dissolved oxygen in the water and releases $CO_2$ simultaneously. $CO_2$ enters the oxygen mass-transfer stir zone through the gas-exchange channels of the perforated partition, and is absorbed by the solution capable of absorbing $CO_2$ in the carbon dioxide absorption tube, so that negative pressure is generated inside the respirator. The respirometer includes a respirometer element which is connected with the respirator, and an oxygen tank which is connected with the respirometer element. The respirator inhales air from the oxygen tank connected with the respirometer element, and an inspiratory rate and a total inspiratory amount are recorded by the respirometer element. Respiratory dynamic parameters of the tested MBBR fillers can be calculated according to the inspiratory rate of oxygen recorded by the respirometer element.

Preferably, the respirometer element is connected with the respirator via a first tube, and the respirometer element is connected with the oxygen tank via a second tube. One end of the first tube is provided with a needle, and the needle is inserted into the headspace cap of the respirator to enter the interior of the respirator.

A measuring method for a respiratory rate of a biofilm is carried out by using the above-mentioned measuring device, and includes the following steps:

S1, putting the MBBR fillers attached with the biofilm into the biofilm reaction zone, adding a water sample to immerse the MBBR fillers in the biofilm reaction zone;

S2, adding the solution capable of absorbing $CO_2$ to the carbon dioxide absorption tube, sealing the biofilm reaction zone and the oxygen mass-transfer stir zone, connecting the respirometer to the interior of the body via a tube, activating the stirring device located in the oxygen mass-transfer stir zone; and S3, acquiring the inspiratory rate and the total inspiratory amount recorded by the respirometer.

Generally, the water sample is effluent from a MBBR culture reactor, or may be a solution prepared to be suitable for the growth of microorganism according to needs. Microorganism attached to the MBBR fillers in the respirator proceeds with a biological reaction in the biofilm reaction zone, consumes the dissolved oxygen in the water and releases $CO_2$ simultaneously. $CO_2$ enters the oxygen mass-transfer stir zone through the gas-exchange channels of the perforated partition, and is absorbed by the solution capable of absorbing $CO_2$ in the carbon dioxide absorption tube through the air vent, so that negative pressure is generated inside the respirator. The respirometer includes a respirometer element which is connected with the respirator, and an oxygen tank which is connected with the respirometer element. The respirator inhales air from the oxygen tank connected with the respirometer element. Water flow in the oxygen mass-transfer stir zone generates whirlpool due to the stirring effect of the stirring device, so that oxygen that is newly supplemented is dissolved in water rapidly. Oxygen-rich water flow enters the biofilm reaction zone through the liquid-exchange channel of the perforated partition, which supplements oxygen consumed by the microbial reaction of the MBBR fillers, so that the microbial reaction continues. The inspiratory rate and the total inspiratory amount are recorded by the respirometer element. Respiratory dynamic characteristics of the biofilm on the tested MBBR fillers can be calculated according to the inspiratory rate of oxygen recorded by the respirometer element.

Compared with the prior art, the beneficial effects of the present invention are as follows.

In a respirator, a measuring device and a measuring method for measuring a respiratory rate of a biofilm provided by the present invention, a perforated partition having a liquid-exchange channel and a gas-exchange channel divides an interior of a body into an oxygen mass-transfer stir zone and a biofilm reaction zone, the oxygen mass-transfer stir zone is provided with a stirring device, MBBR fillers are placed in the biofilm reaction zone, so that the stirring device would not be interfered by the MBBR fillers, and the biofilm would not be scraped off the MBBR fillers by the stirring device either, thereby avoiding an irreversible damage to the biofilm. Such configuration on one hand ensures sufficient gas-liquid exchange of the oxygen mass-transfer stir zone and the biofilm reaction zone, and on the other hand prevents damage to the biofilm on the MBBR fillers by the stirring device, ensuring that a mass-transfer power between the oxygen of the biofilm on the fillers and nutrient substances would not vary with an experimental period. The respiratory dynamic characteristics of the biofilm on the fillers are determined in situ without damage. Therefore, the respirator, the measuring device and the measuring method for measuring a respiratory rate of a biofilm provided by the present invention achieve an in situ determination for a biofilm respiratory rate, with simpler and more rapid measuring process, and more accurate and efficient test results. The test results are conducive to understand the growth status of the biofilm on the MBBR fillers more accurately and truly.

DESCRIPTION OF SPECIFIC EMBODIMENTS OF THE INVENTION

The present invention is further described in detail in combination with specific implementations as below, but the present invention is not limited thereto. Unless otherwise specified, reagents and methods related to the examples are conventional reagents and methods in the art.

Identical or similar reference numbers in the accompanying drawings of the examples in the present invention correspond to the identical or similar components. In the description of the present invention, it should be understood that an orientation or positional relationship which is indicated by terms such as "upper", "lower", "left", "right", "top", "bottom", "inside" and "outside" is the orientation or positional relationship based on the accompanying drawings, merely for describing the present invention conveniently and simplifying the description, rather than indicating or implying that the described device or element has a specific orientation, or is configured or operated in a specific orientation. Thus, the terms used to describe the positional relationship in the accompanying drawings are for illustrative purposes only and are not to be construed as limiting the present invention.

Additionally, terms such as "first", "second" and the like are merely for descriptive purposes, and are mainly used to distinguish a different device, element or component (the specific type and configuration may be identical or different), and not to indicate or imply a relative importance and numbers of the mentioned device, element or component, and thus not to be construed as indicating or implying the relative importance.

Example 1

Figure 1:
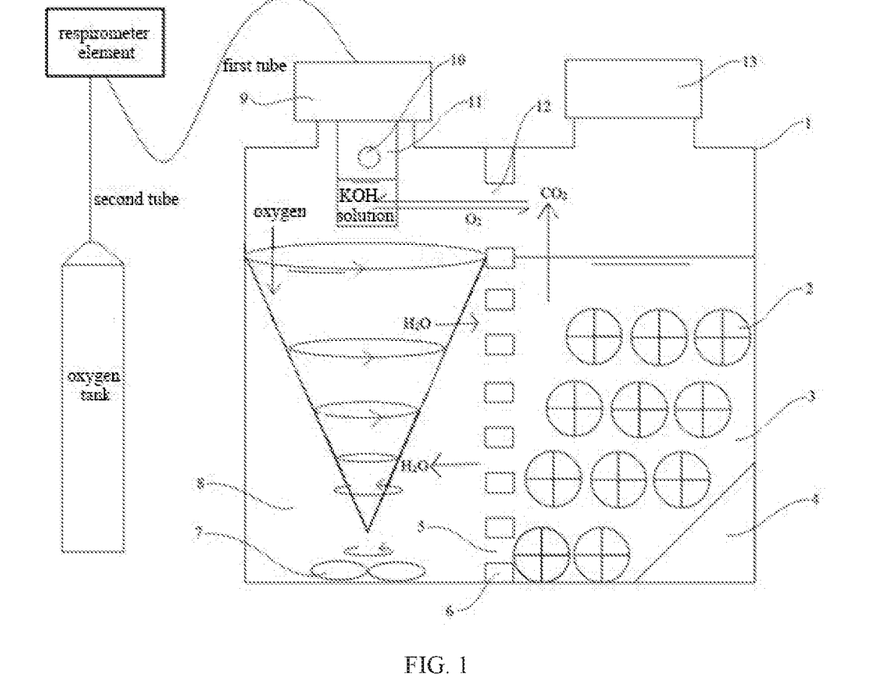
FIG. 1 is a schematic diagram of a measuring device formed by connecting a respirator for measuring a respiratory rate of a biofilm and a respirometer for measuring an oxygen-absorption rate according to Example 1.
Figure 2:
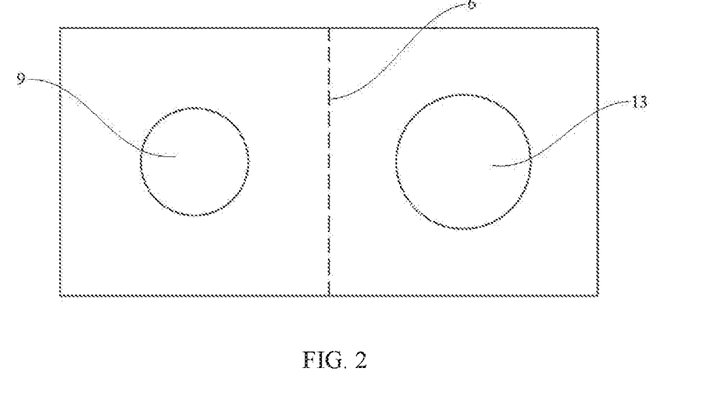
FIG. 2 is a top view of the respirator according to Example 1.

FIG. 1 is a schematic diagram of a measuring device formed by connecting a respirator for measuring a respiratory rate of a biofilm and a respirometer for measuring an oxygen-absorption rate according to Example 1. FIG. 2 is a top view of the respirator according to Example 1. As shown in FIG. 1 and FIG. 2, a respirator for measuring a respiratory rate of a biofilm according to the present invention includes a body 1, a carbon dioxide absorption tube 11 and a perforated partition 6 disposed in an interior of the body 1. The perforated partition 6 divides the interior of the body 1 into an oxygen mass-transfer stir zone 8 and a biofilm reaction zone 3, the oxygen mass-transfer stir zone 8 is provided with a stirring device 7, the biofilm reaction zone 3 is used for placing MBBR fillers 2. The carbon dioxide absorption tube 11 is provided with an air vent 10 and contains a solution capable of absorbing $CO_2$, to absorb the $CO_2$ within the body 1. The perforated partition 6 has a first hole and a second hole, the first hole is located at a middle portion and a lower portion of the perforated partition 6 and acts as a liquid-exchange channel 5, the second hole is located at an upper portion of the perforated partition 6 and acts as a gas-exchange channel 12, and the oxygen mass-transfer stir zone 8 is communicated with the biofilm reaction zone 3 through the liquid-exchange channel 5 and the gas-exchange channel 12. The body 1 is provided with a first opening and a second opening, the first opening corresponds to the oxygen mass-transfer stir zone 8, and the second opening corresponds to the biofilm reaction zone 3. The first opening is provided with a headspace cap 9 for sealing, and the second opening is provided with a sealing cap 13 for sealing. The carbon dioxide absorption tube 11 is located in the interior of the body 1 and connected to the headspace cap 9. A bottom of the biofilm reaction zone 3 is further provided with a corner sloping board 4 at a corner of the body 1. The body 1 is cuboid or cylindrical. The stirring device 7 is a magnetic stirrer located at a bottom of the oxygen mass-transfer stir zone 8.

The respirator and a respirometer compose a measuring device. The respirometer includes a respirometer element and an oxygen tank, and the respirometer element is connected with the respirator via a first tube and connected with the oxygen tank via a second tube. One end of the first tube is provided with a needle, and the needle is inserted into the headspace cap 9 of the body 1 to enter the interior of the body 1.

Figure 3:
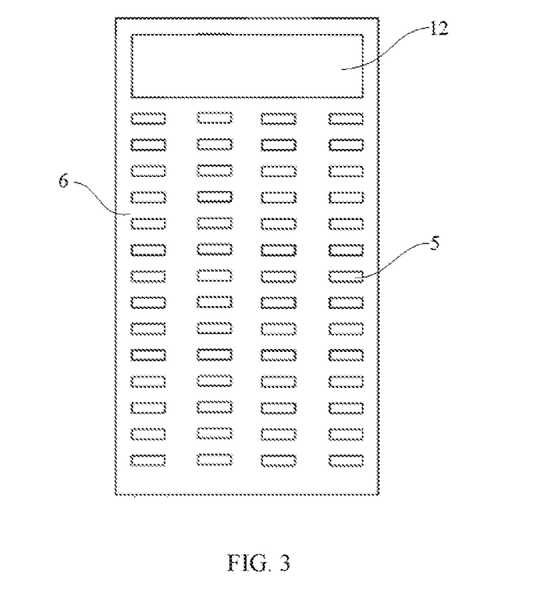
FIG. 3 is a schematic diagram of a perforated partition according to the present invention.

FIG. 3 is a schematic diagram of a perforated partition 6 according to the present invention. As shown in FIG. 3, the first hole includes a plurality of first holes, and the liquid-exchange channel 5 is evenly distributed at the middle portion and the lower portion of the perforated partition 6. The liquid-exchange channel has a relatively small size to prevent the MBBR fillers 2 in the biofilm reaction zone 3 from entering the oxygen mass-transfer stir zone 8, while the gas-exchange channel 12 has a relatively large size to prevent forming a liquid film that prohibits the gas exchange.

A method for measuring a respiratory rate of a biofilm by using the above-mentioned measuring device includes the following steps:

S1, putting the MBBR fillers 2 attached with the biofilm into the biofilm reaction zone 3, adding a water sample to immerse the MBBR fillers 2 in the biofilm reaction zone 3;

S2, adding a KOH solution capable of absorbing $CO_2$ to the carbon dioxide absorption tube 11, sealing the biofilm reaction zone 3 and the oxygen mass-transfer stir zone 8, connecting the respirometer element to the interior of the body via the first tube and to the oxygen tank via the second tube, activating the stirring device 7 located in the oxygen mass-transfer stir zone 8; and S3, acquiring an inspiratory rate and a total inspiratory amount recorded by the respirometer element.

Microorganism attached to the MBBR fillers 2 proceeds with a biological reaction in the biofilm reaction zone 3, consumes the dissolved oxygen in the water and releases $CO_2$ simultaneously. $CO_2$ enters the oxygen mass-transfer stir zone 8 through the gas-exchange channels 12 of the perforated partition 6, and is absorbed by the KOH solution capable of absorbing $CO_2$ in the carbon dioxide absorption tube 11 through the air vent, so that negative pressure is generated inside the respirator. The respirator inhales air from the oxygen tank connected with the respirometer element. Water flow in the oxygen mass-transfer stir zone 8 generates whirlpool due to the stirring effect of the stirring device 7, so that oxygen that is newly supplemented is dissolved in water rapidly. Oxygen-rich water flow enters the biofilm reaction zone 3 through the liquid-exchange channel 5 of the perforated partition 6, which supplements oxygen consumed by the microbial reaction of the MBBR fillers 2, so that the microbial reaction continues. The inspiratory rate and the total inspiratory amount of the respirator are recorded by the respirometer element. Respiratory dynamic characteristics of the biofilm on the tested MBBR fillers 2 can be calculated according to the inspiratory rate of oxygen recorded by the respirometer element.

In the respirator, the measuring device and the measuring method for measuring a respiratory rate of a biofilm provided by the present invention, a perforated partition 6 having a liquid-exchange channel 5 and a gas-exchange channel 12 divides an interior of a body 1 into an oxygen mass-transfer stir zone 8 and a biofilm reaction zone 3, the oxygen mass-transfer stir zone 8 is provided with a stirring device 7, the MBBR fillers 2 are placed in the biofilm reaction zone 3, so that the stirring device 7 would not be interfered by the MBBR fillers 2, and the biofilm would not be scraped off the MBBR fillers 2 by the stirring device 7 either, thereby avoiding an irreversible damage to the biofilm. Such configuration on one hand ensures sufficient gas-liquid exchange of the oxygen mass-transfer stir zone 8 and the biofilm reaction zone 3, and on the other hand prevents damage to the biofilm on the MBBR fillers 2 by the stirring device 7. The respiratory dynamic characteristics of the biofilm on the fillers can be determined in situ without damage. Therefore, the respirator for measuring a respiratory rate of a biofilm, the measuring device and the measuring method provided by the present invention achieve an in situ determination for a biofilm respiratory rate, with simpler and more rapid measuring process, and more accurate and efficient test results. The test results are conducive to understand the growth status of the biofilm on the MBBR fillers 2 more accurately and truly.

Example 2

Figure 4:
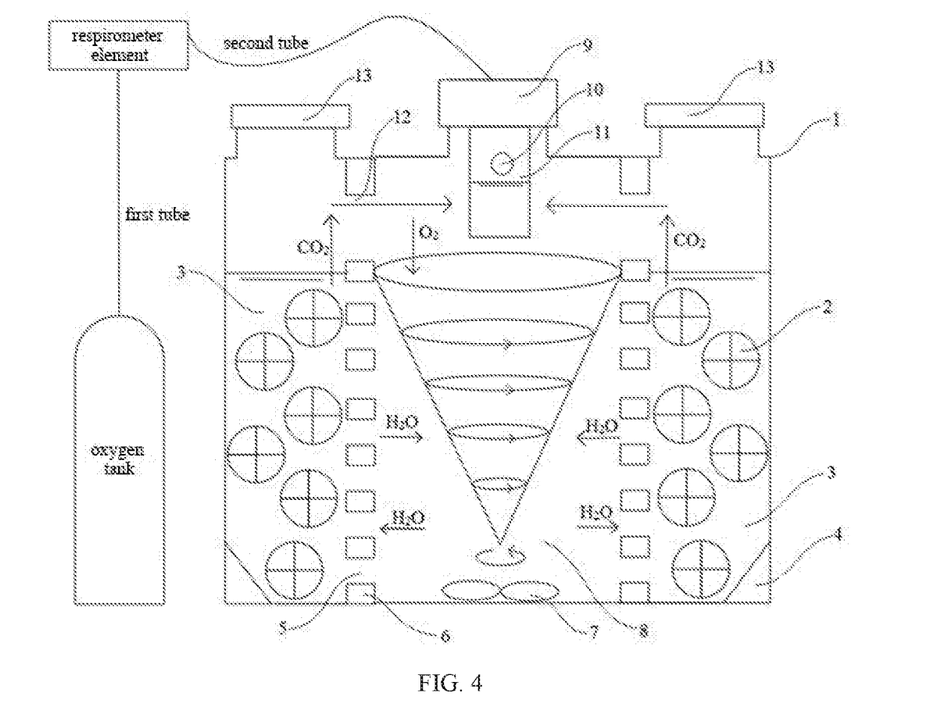
FIG. 4 is a schematic diagram of a measuring device formed by connecting a respirator for measuring a respiratory rate of a biofilm and a respirometer for measuring an oxygen-absorption rate according to Example 2 and Example 3.
Figure 5:
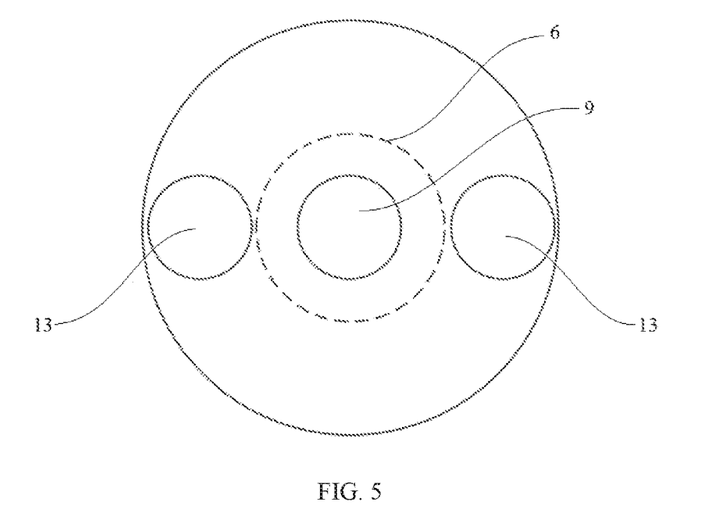
FIG. 5 is a top view of the respirator according to Example 2.

FIG. 4 is a schematic diagram of a measuring device formed by connecting a respirator for measuring a respiratory rate of a biofilm and a respirometer for measuring an oxygen-absorption rate according to Example 2 and Example 3. FIG. 5 is a top view of the respirator according to Example 2. The present example is the second example of the respirator according to the present invention. As shown in FIG. 4 and FIG. 5, the differences from Example 1 lie in that: in the present example, the body 1 is cylindrical; the perforated partition 6 is cylindrical, and an interior of the cylindrical perforated partition 6 is the oxygen mass-transfer stir zone 8, between an exterior of the cylindrical perforated partition 6 and the body 1 is the biofilm reaction zone 3; the perforated partition 6 is located in the middle of the body 1, the first opening corresponds to the oxygen mass-transfer stir zone 8 in the interior of the cylindrical perforated partition; the body 1 is provided with two second openings, the two second openings correspond to the biofilm reaction zone 3 in the exterior of the cylindrical perforated partition; and the two second openings are each provided with a sealing cap 13 for sealing.

$CO_2$ which is released by the microbial reaction on the MBBR fillers 2 in the biofilm reaction zone 3 enters the oxygen mass-transfer stir zone 8 in the interior of the cylindrical perforated partition from the exterior of the cylindrical perforated partition. Whirlpool of water flow in the oxygen mass-transfer stir zone 8 is formed due to the stirring device in the respirator, and water flows all around. The respirator of the present example is conducive to mixing the MBBR fillers 2 and the water flow, thereby improving a mass-transfer effect.

Example 3

Figure 6:
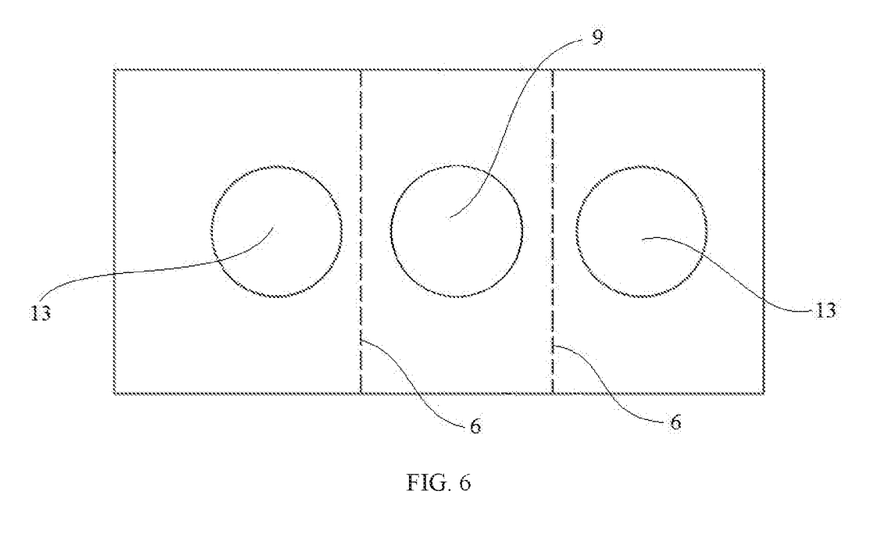
FIG. 6 is a top view of the respirator according to Example 3.

FIG. 4 is a schematic diagram of a measuring device formed by connecting a respirator for measuring a respiratory rate of a biofilm and a respirometer for measuring an oxygen-absorption rate according to Example 2 and Example 3. FIG. 6 is a top view of the respirator according to Example 3. The present example is the third example of the respirator of the present invention. As shown in FIG. 4 and FIG. 6, the differences from Example 1 lie in that: the perforated partition 6 includes two perforated partition 6, between the two perforated partitions 6 is the oxygen mass-transfer stir zone 8, between the perforated partition 6 and the body 1 is the biofilm reaction zone 3; the body 1 is provided with two second openings, the two second openings correspond to two biofilm reaction zones 3; and the two second openings are each provided with a sealing cap 13 for sealing.

$CO_2$ which is released by the microbial reaction on the MBBR fillers 2 in the biofilm reaction zones 3 at either side enters the oxygen mass-transfer stir zone 8 in the middle from the biofilm reaction zones 3 at either side. Whirlpool of water flow in the oxygen mass-transfer stir zone 8 is formed due to the stirring device in the respirator, and water flows all around. The respirator of the present example is conducive to mixing the MBBR fillers 2 and the water flow, thereby improving a mass-transfer effect.

Apparently, the above-mentioned examples of the present invention are merely illustrative examples for the purpose of describing the present invention clearly, and are not intended to limit the implementation of the present invention. For those skilled in the art, modification or variation in other different forms can also be made based on the above description. There's no need or no way to exhaust all of the implementations. Any modifications, equivalent substitutions and improvements made within the spirit and scope of the present invention are intended to be included within the scope of protection of the claims in the present invention.

What is claimed is:

1. A respirator for measuring a respiratory rate of a biofilm, characterized in that, the respirator comprises a body (1), a carbon dioxide absorption tube (11) disposed in an interior of the body and at least one perforated partition (6) disposed in an interior of the body (1);
    the at least one perforated partition (6) divides the interior of the body (1) into an oxygen mass-transfer stir zone (8) and at least one biofilm reaction zone (3), the oxygen mass-transfer stir zone (8) is provided with a stirring device (7), the at least one biofilm reaction zone (3) is used for placing MBBR fillers (2);
    the carbon dioxide absorption tube (11) is provided with an air vent (10) and contains a solution, configured to absorb $CO_2$ within the body (1);
    the at least one perforated partition (6) has a plurality of first holes and a second hole, the plurality of first holes is located at a middle portion and a lower portion of the at least one perforated partition (6) and defining a plurality of liquid-exchange channels (5), the second hole is located at an upper portion of the at least one perforated partition (6) and defining a gas-exchange channel (12), and the oxygen mass-transfer stir zone (8) is in communication with the at least one biofilm reaction zone (3) through the plurality of liquid-exchange channels (5) and the gas-exchange channel (12);
    a first opening and at least one second opening provided on the body, the first opening corresponds to the oxygen mass-transfer stir zone (8), the at least one second opening corresponds to the at least one biofilm reaction zone (3); and
    a headspace cap (9) coupled to the first opening and configured to seal the first opening, and at least one sealing cap (13) coupled to the at least one second opening and configured to seal the at least one second opening, and
    wherein the carbon dioxide absorption tube (11) is coupled to the headspace cap (9).

2. The respirator according to claim 1, wherein the at least one perforated partition (6) comprises two perforated partitions (6), wherein the at least one biofilm reaction zone (3) includes two biofilm reaction zones, between the two perforated partitions (6) is the oxygen mass-transfer stir zone (8), and between the perforated partition (6) and the body (1) is the two biofilm reaction zones (3).

3. The respirator according to claim 2, wherein the at least one second opening includes two second openings, wherein the at least one sealing cap includes two sealing caps, the two second openings correspond to the two biofilm reaction zones (3) respectively, and the two second openings are each provided with a sealing cap (13) of the two sealing caps for sealing the two second openings respectively.

4. The respirator according to claim 1, wherein a bottom of the at least one biofilm reaction zone (3) is further provided with a corner sloping board (4) at a corner of the body (1).

5. The respirator according to claim 1, wherein the body (1) is cuboid or cylindrical.

6. The respirator according to claim 1, wherein the plurality of liquid-exchange channels (5) is evenly distributed at the middle portion and the lower portion of the at least one perforated partition (6).

7. The respirator according to claim 1, wherein the stirring device (7) is a magnetic stirrer located at a bottom of the oxygen mass-transfer stir zone (8).

8. A measuring device for a respiratory rate of a biofilm, characterized in that, the measuring device comprises a respirometer for measuring an oxygen-absorption rate and the respirator according to claim 1, and the respirometer is communicated with an interior of the respirator.

9. A measuring method for a respiratory rate of a biofilm, characterized in that, comprising the following steps:
    providing the measuring device according to claim 8;
    putting the MBBR fillers (2) attached with the biofilm into the at least one biofilm reaction zone (3), adding a water sample to immerse the MBBR fillers (2) in the at least one biofilm reaction zone (3);
    adding the solution capable of absorbing $CO_2$ to the carbon dioxide absorption tube (11), sealing the at least one biofilm reaction zone (3) and the oxygen mass-transfer stir zone (8), connecting the respirometer to the interior of the body (1) via a tube, activating the stirring device (7) located in the oxygen mass-transfer stir zone (8); and
    acquiring an inspiratory rate and a total inspiratory amount recorded by the respirometer.

10. A respirator for measuring a respiratory rate of a biofilm, characterized in that, the respirator comprises a body (1), a carbon dioxide absorption tube (11) disposed in an interior of the body and a perforated partition (6) disposed in an interior of the body (1);
    a perforated partition (6) divides the interior of the body (1) into an oxygen mass-transfer stir zone (8) and a biofilm reaction zone (3), the oxygen mass-transfer stir zone (8) is provided with a stirring device (7), the biofilm reaction zone (3) is used for placing MBBR fillers (2);
    the carbon dioxide absorption tube (11) is provided with an air vent (10) and contains a solution configured to absorb $CO_2$ within the body (1);
    the perforated partition (6) has a plurality of first holes and a second hole, the plurality of first holes is located at a middle portion and a lower portion of the perforated partition (6) and defining a plurality of liquid-exchange channels (5), the second hole is located at an upper portion of the perforated partition (6) and defining a gas-exchange channel (12), and the oxygen mass-transfer stir zone (8) is in communication with the biofilm reaction zone (3) through the a plurality of liquid-exchange channels (5) and the gas-exchange channel (12);
a first opening and a second opening provided on the body, the first opening corresponds to the oxygen mass-transfer stir zone (8), the second opening corresponds to the biofilm reaction zone (3); and
a headspace cap (9) coupled to the first opening and configured to seal the first opening, and sealing cap (13) coupled to the second opening and configured to seal the second opening, and
wherein the carbon dioxide absorption tube (11) is coupled to the headspace cap (9).

11. The respirator according to claim 10, wherein the perforated partition (6) is a cylindrical perforated partition (6) and located at a middle portion of the body (1), an interior of the cylindrical perforated partition (6) defines the oxygen mass-transfer stir zone (8), and between an exterior of the cylindrical perforated partition (6) and the body (1) defines the biofilm reaction zone (3).

12. The respirator according to claim 10, wherein a bottom of the biofilm reaction zone (3) is further provided with a corner sloping board (4) at a corner of the body (1).

13. The respirator according to claim 10, wherein the body (1) is cuboid or cylindrical.

14. The respirator according to claim 10, wherein the first hole comprises a plurality of first holes, and the plurality of liquid-exchange channels (5) is evenly distributed at the middle portion and the lower portion of the perforated partition (6).

15. The respirator according to claim 10, wherein the stirring device (7) is a magnetic stirrer located at a bottom of the oxygen mass-transfer stir zone (8).

16. A measuring device for a respiratory rate of a biofilm, characterized in that, the measuring device comprises a respirometer for measuring an oxygen-absorption rate and the respirator according to claim 10, and the respirometer is communicated with an interior of the respirator.

17. A measuring method for a respiratory rate of a biofilm, characterized in that, comprising the following steps:
providing the measuring device according to claim 16;
putting the MBBR fillers (2) attached with the biofilm into the biofilm reaction zone (3), adding a water sample to immerse the MBBR fillers (2) in the biofilm reaction zone (3);
adding the solution capable of absorbing $CO_2$ to the carbon dioxide absorption tube (11), sealing the biofilm reaction zone (3) and the oxygen mass-transfer stir zone (8), connecting the respirometer to the interior of the body (1) via a tube, activating the stirring device (7) located in the oxygen mass-transfer stir zone (8); and
acquiring an inspiratory rate and a total inspiratory amount recorded by the respirometer.

* * * * *